(12) United States Patent
Spence et al.

(10) Patent No.: US 7,835,502 B2
(45) Date of Patent: Nov. 16, 2010

(54) TARGET PEDESTAL ASSEMBLY AND METHOD OF PRESERVING THE TARGET

(75) Inventors: David Arthur Spence, Hartland, WI (US); Richard Cary Schmidt, Verona, WI (US)

(73) Assignee: Tomotherapy Incorporated, Madison, WI (US)

( * ) Notice: Subject to any disclaimer, the term of this patent is extended or adjusted under 35 U.S.C. 154(b) by 0 days.

(21) Appl. No.: 12/369,449

(22) Filed: Feb. 11, 2009

(65) Prior Publication Data

US 2010/0202593 A1 Aug. 12, 2010

(51) Int. Cl.
*H01J 35/08* (2006.01)
*H05G 1/00* (2006.01)

(52) U.S. Cl. .................. 378/143; 378/204
(58) Field of Classification Search .......... 378/119, 378/124, 125, 141, 143, 144, 199, 200, 204
See application file for complete search history.

(56) References Cited

U.S. PATENT DOCUMENTS

| | | | |
|---|---|---|---|
| 4,323,780 A | 4/1982 | Tombaugh et al. | |
| 4,477,921 A * | 10/1984 | Armini et al. | 378/34 |
| 4,737,647 A | 4/1988 | Stieber | |
| 5,052,034 A | 9/1991 | Schuster | |
| 5,332,908 A | 7/1994 | Weidlich | |
| 5,734,168 A | 3/1998 | Yao | |
| 5,757,885 A | 5/1998 | Yao et al. | |
| 5,940,469 A | 8/1999 | Hell et al. | |
| 6,141,400 A | 10/2000 | Schardt et al. | |
| 6,407,505 B1 | 6/2002 | Bertsche | |
| 6,463,123 B1 | 10/2002 | Korenev | |
| 6,465,957 B1 | 10/2002 | Whitham et al. | |
| 6,487,274 B2 | 11/2002 | Bertsche | |
| 6,493,424 B2 | 12/2002 | Whitham | |
| 6,882,705 B2 | 4/2005 | Egley et al. | |
| 6,937,693 B2 | 8/2005 | Svatos | |
| 7,022,994 B2 | 4/2006 | Fuchs et al. | |
| 2006/0133568 A1 | 6/2006 | Moore | |

* cited by examiner

*Primary Examiner*—Irakli Kiknadze
(74) *Attorney, Agent, or Firm*—Michael Best & Friedrich LLP (57) ABSTRACT

An x-ray target pedestal assembly and a method of protecting the x-ray target from breaking down as a result of the extreme heat that is produced when an electron beam is aimed at the target to produce x-rays. The target is submerged in cooling fluid and is rotated by a constant flow of the cooling fluid over and around the target in order to dissipate heat. The fluid is guided by integrated flow diverters in the target cover. The target may also be protectively coated either in its entirety or along the electron beam path in order to further protect it from the heat of the electron beam impact or from breakdown as a result of attack of free radicals or other chemically reactive components of the cooling fluid which are produced in the extreme target environment.

52 Claims, 11 Drawing Sheets

TARGET PEDESTAL ASSEMBLY AND METHOD OF PRESERVING THE TARGET

FIELD OF THE INVENTION

This invention relates to external radiotherapy treatment systems and methods. More specifically, the invention relates to an x-ray target pedestal assembly and to a method of preserving the target when it is exposed to an electron beam to produce x-ray radiation.

BACKGROUND OF THE INVENTION

Medical equipment for radiation therapy treats tumorous tissue with high-energy radiation. One source of therapeutic radiation is high-energy x-rays. To produce high-energy x-rays, an electron beam is emitted from a linear accelerator (linac) and is aimed at a solid target. The target is bombarded with the electrons from the beam, and high-energy photons (x-rays) are produced as a result of the interaction between the fast moving electrons and the atomic structure of the target. The deceleration of electrons caused by the interaction of the electrons with the material of the target creates the x-rays in a process known as bremsstrahlung. The resulting x-rays are then collimated and directed to the treatment area.

SUMMARY OF THE INVENTION

The target is usually made from a refractory metal with a very high atomic number and density and with a high melting point. Suitable target materials include tungsten, molybdenum, and rhenium. The intensity of x-ray radiation produced is a function of properties of the material including the atomic number of the target material. The target can be integral to the linac, or it may be removable if it is housed outside of the linac's vacuum environment. The target may be either rotating or stationary and may be a variety of shapes. The x-ray spectrum produced will vary with the thickness of the target and with the energy of the electron beam, as electrons progressively lose energy as they pass through the target.

Not all of the electron beam's energy is converted into x-rays. Large amounts of thermal energy are created from the interaction of the high-energy electrons with the target. As such, a cooling mechanism is typically used to preserve the target material by protecting the target from heat stresses and preventing the target from reaching its melting point. Rotating targets are often used so that the electron beam does not consistently contact the same portion of the target.

The target may be cooled by any number of coolants, or cooling media, as keeping the target submerged in a coolant boosts the heat transfer away from the target. Water is the most benign coolant that can be subjected to the radiation of the target environment. However, incident radiation causes oxidation, breaking down water molecules to produce free radical hydrogen and oxygen atoms that will attack and degrade the target material. The target material will break down or become unstable over time as a result of the extreme environment created by the interaction of the electrons with the cooling fluid. As the target material breaks down, it becomes thinner and its photon conversion capacity is diminished. Therefore, target life is limited, and the target must be replaced from time to time.

The present invention relates to a radiation therapy x-ray target pedestal assembly designed to preserve the life of the x-ray target and a method for protectively coating the target to extend the target life. An electron beam contacts the target to generate x-rays, and the target rotates around a central axis to dissipate the resulting heat. The target is submerged in a cooling fluid, and the cooling fluid flow is directed to and around the target by integrated flow diverters in the target cover, which guide the flow such that the target passively rotates, distributing the heat around the target. The target may be protected from chemical corrosion if a protective coating is applied to the target, either completely encasing the target or protecting a portion of the target. The target pedestal assembly allows the target to rotate freely about a replaceable rotational pin at its central axis, guides coolant flow to and around the target, and allows for fluid cooling of the target by maintaining consistent rotation of the target and consequently extends target life.

In one embodiment, the invention provides target pedestal assembly for a radiation delivery device. The target pedestal assembly comprises a pedestal weldment coupled to a linear accelerator of the radiation delivery device, the pedestal weldment including a first recessed area and a first channel adjacent to the first recessed area, the channel including a first flow diverter at a first end of the channel and a second flow diverter at a second end of the channel; a cover coupled to the pedestal weldment, the cover including a second recessed area complementary to the first recessed area and a second channel complementary to the first channel; and a target rotationally coupled to the pedestal weldment and the cover and positioned between the first recessed area and the second recessed area, a portion of the target positioned between the first channel and the second channel, the target being protected with a material sufficient to reduce chemical reactivity between the target and cooling medium flowing in the channel.

In another embodiment, the invention provides a target pedestal assembly for a radiation delivery device. The target pedestal assembly comprises a housing coupled to a linear accelerator of the radiation delivery device, the housing defining a cavity and a channel adjacent to the cavity, the channel including a first flow diverter at a first end of the channel and a second flow diverter at a second end of the channel; a target positioned within the cavity and rotationally coupled to the housing, a portion of the target positioned within the channel, the target including a serrated edge arranged around a perimeter of the target; and a cooling medium positioned within the cavity and the channel, the target being protected with a material sufficient to reduce chemical reactivity between the target and the cooling medium.

In yet another embodiment, the invention provides a target pedestal assembly for a radiation delivery device. The target pedestal assembly comprises a housing including a cavity and a cooling medium flowing within the cavity; and a target comprising tungsten and positioned within the cavity, the target submerged in the cooling medium, the target being protected with a material sufficient to reduce chemical reactivity between the target and the cooling medium.

DETAILED DESCRIPTION OF THE INVENTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

In addition, it should be understood that embodiments of the invention include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

Figure 1:
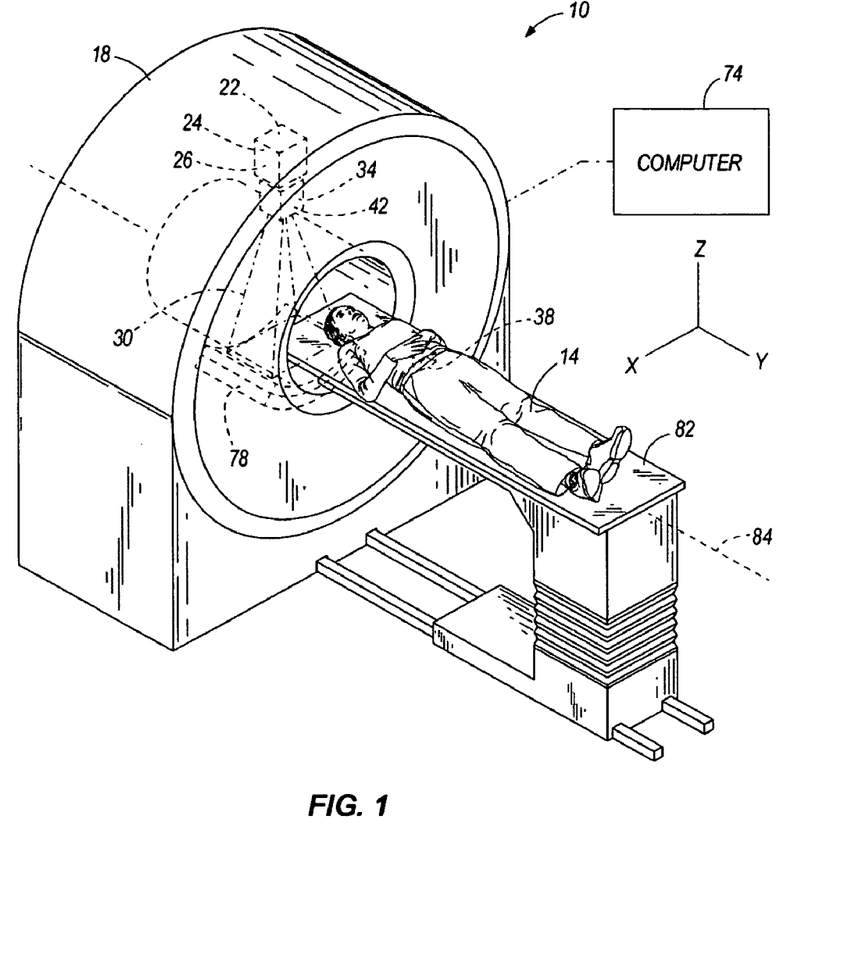
FIG. 1 is a perspective view of a radiation therapy treatment system.

FIG. 1 illustrates a radiation therapy treatment system 10 that can provide radiation therapy to a patient 14. The radiation therapy treatment can include photon-based radiation therapy, brachytherapy, electron beam therapy, proton, neutron, or particle therapy, or other types of treatment therapy. The radiation therapy treatment system 10 includes a gantry 18. The gantry 18 can support a radiation module 22, which can include a radiation source 24 and a linear accelerator 26 (a.k.a. "a linac") operable to generate a beam 30 of radiation. Though the gantry shown in the drawings is a ring gantry, i.e., it extends through a full 360° arc to create a complete ring or circle, other types of mounting arrangements may also be employed. For example, a C-type, partial ring gantry, or robotic arm could be used. Any other framework capable of positioning the radiation module 22 at various rotational and/or axial positions relative to the patient 14 may also be employed. In addition, the radiation source 24 may travel in a path that does not follow the shape of the gantry 18. For example, the radiation source 24 may travel in a non-circular path even though the illustrated gantry 18 is generally circular-shaped. The gantry 18 of the illustrated embodiment defines a gantry aperture 32 into which the patient 14 moves during treatment.

The radiation module 22 can also include a modulation device 34 operable to modify or modulate the radiation beam 30. The modulation device 34 provides the modulation of the radiation beam 30 and directs the radiation beam 30 toward the patient 14. Specifically, the radiation beam 30 is directed toward a portion 38 of the patient. Broadly speaking, the portion may include the entire body, but is generally smaller than the entire body and can be defined by a two-dimensional area and/or a three-dimensional volume. A portion or area desired to receive the radiation, which may be referred to as a target or target region, is an example of a region of interest. Such modulation is sometimes referred to as intensity modulated radiation therapy ("IMRT"). Another type of region of interest is a region at risk. If a portion includes a region at risk, the radiation beam is preferably diverted from the region at risk.

The system 10 can also include a patient support, shown as a couch 82, operable to support at least a portion of the patient 14 during treatment and a drive system 86 operable to manipulate the location of the couch 82 based on instructions provided by the computer 74. The couch 82 moves along at least one axis 84 in the x, y, or z directions. In other embodiments of the invention, the patient support can be a device that is adapted to support any portion of the patient's body. The patient support is not limited to having to support the entire patient's body. The drive system 86 can be controlled by the computer 74.

Figure 2:
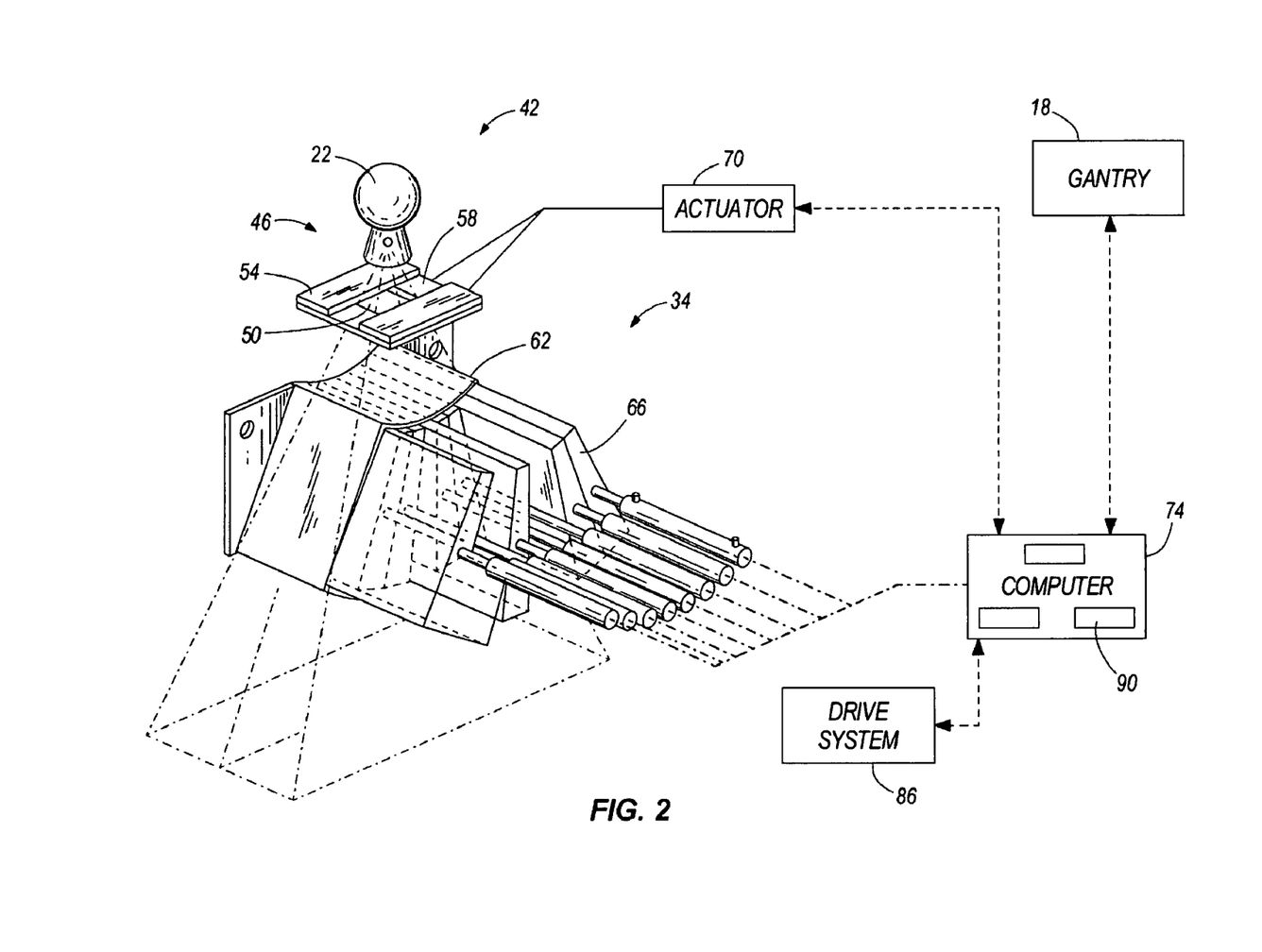
FIG. 2 is a perspective view of a multi-leaf collimator that can be used in the radiation therapy treatment system illustrated in FIG. 1.

The computer 74, illustrated in FIGS. 1 and 2, includes an operating system for running various software programs and/or a communications application. In particular, the computer 74 can include a software program(s) 90 that operates to communicate with the radiation therapy treatment system 10.

Figure 3:
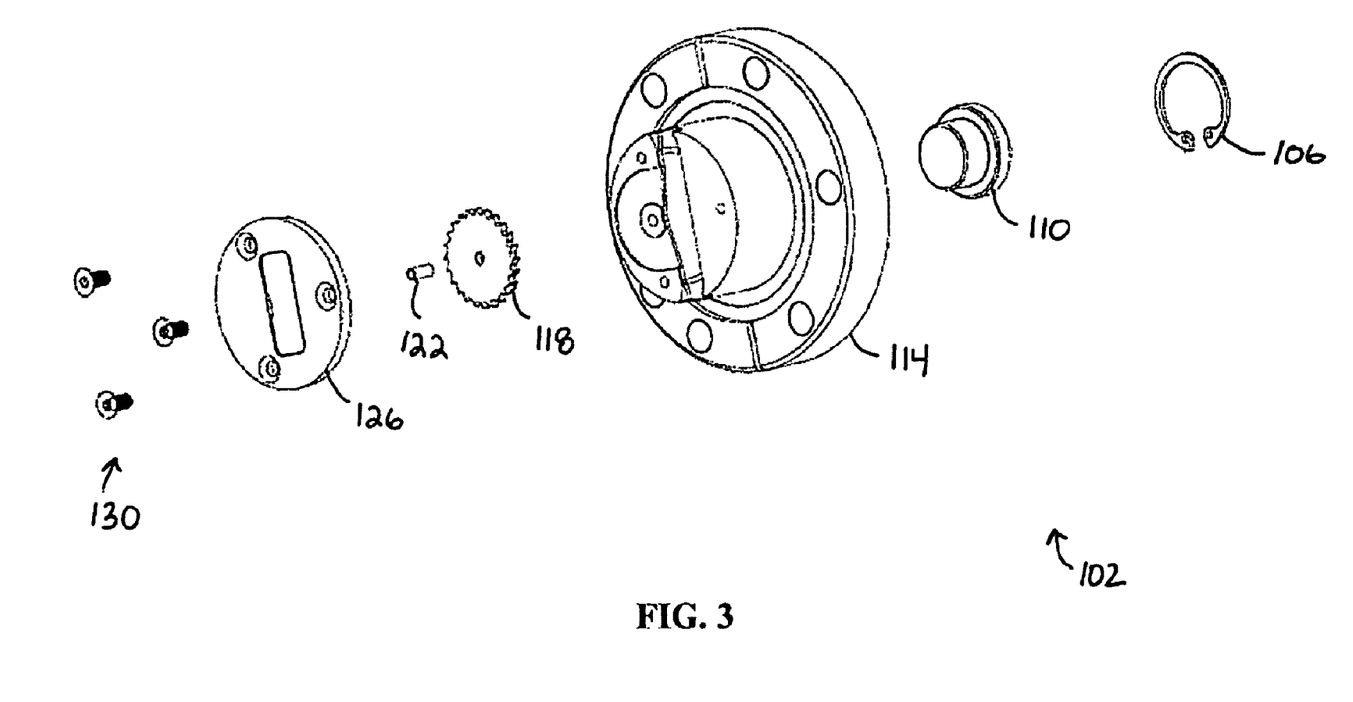
FIG. 3 is a perspective view of the expanded target pedestal assembly.
Figure 4:
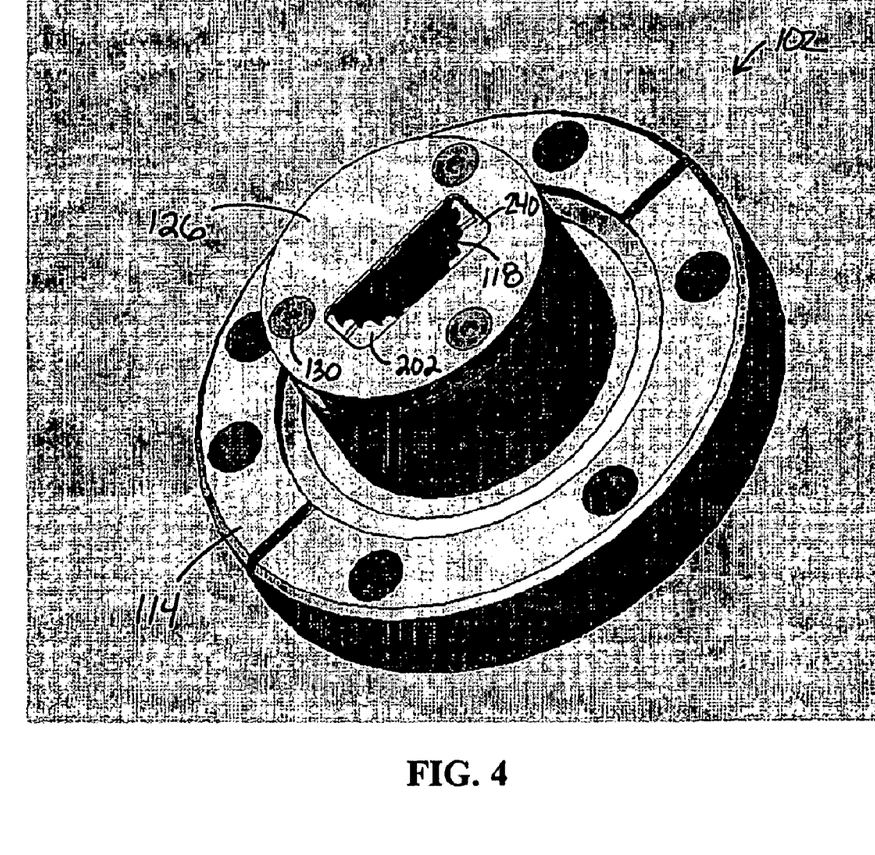
FIG. 4 is a perspective view of the target pedestal assembly.

FIGS. 3-4 illustrate a target pedestal assembly 102 according to one embodiment of the present invention. The pedestal assembly 102 allows for consistent rotation of a fluid-cooled x-ray target. The target pedestal assembly 102 allows for improved rotation of the target and provides an environment for the target that is conducive to the dissipation of heat away from the target. The pedestal assembly 102 can be composed of metal and can vary in shape. The target pedestal assembly 102 allows for the implementation of several target-cooling techniques, including guided fluid flow, consistent rotation of the target, and protection of the target from extreme heat and attack from chemically active components in the cooling medium or fluid. Such chemically active components may include decomposition products such as free radicals. Moreover, the cooling medium or fluid may be in liquid or gaseous phases, or a combination thereof.

The target pedestal assembly 102 includes an internal snap ring 106, an electron filter 110, a pedestal subassembly or housing 114, a target 118, a rotational pin 122, a target cover 126, and a plurality of fasteners (e.g., screws) 130 to attach the target cover 126 to the pedestal weldment 114.

The internal snap ring 106 is constructed of a suitable material, such as stainless steel, that resists corrosion and is of the type used for pieces of similar application. The internal snap ring 106 holds the electron filter 110 in place within the pedestal weldment 114. The snap ring 106 is removable and replaceable. Because the snap ring 106 is removable, the electron filter 110 is replaceable.

Figure 5:
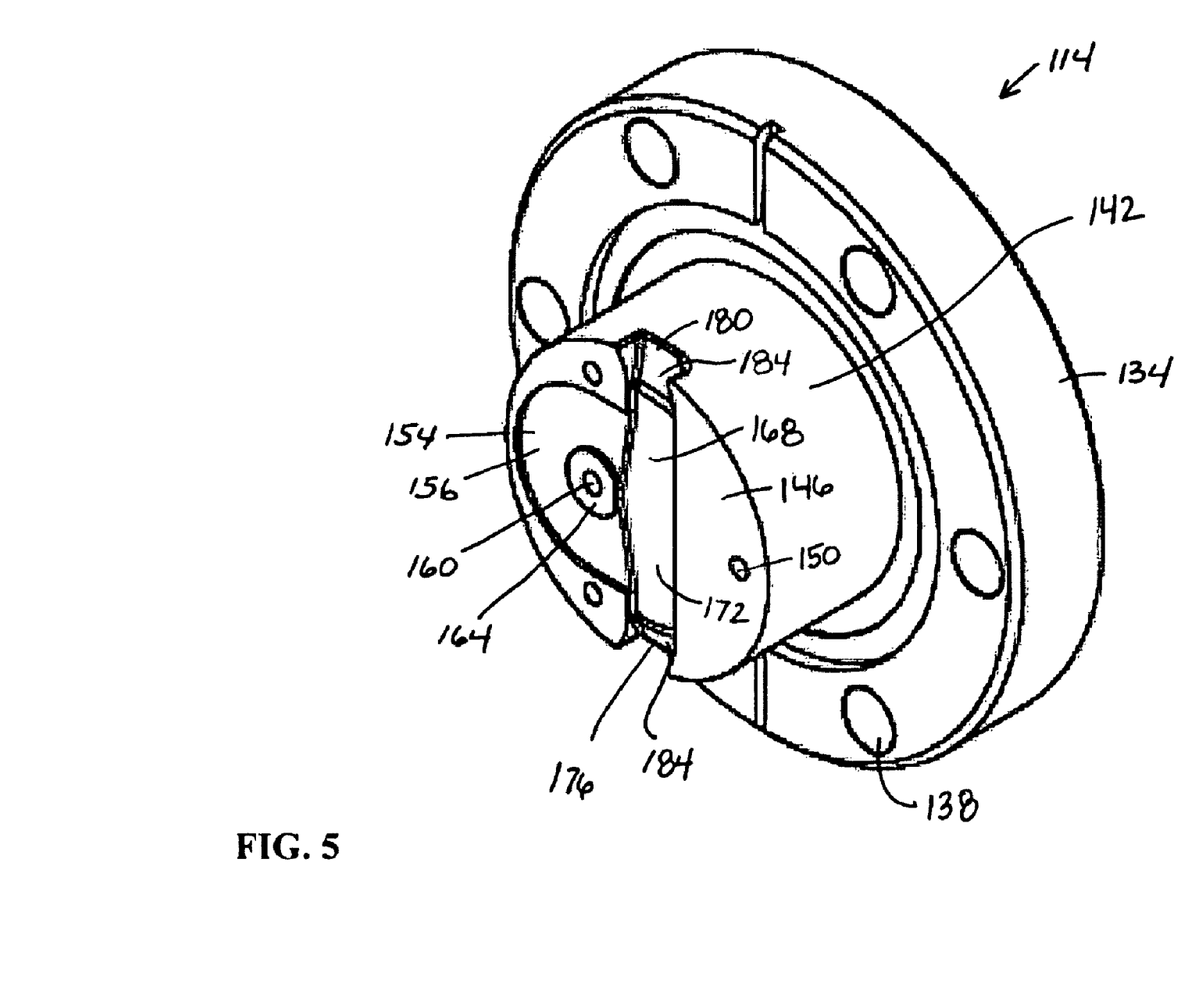
FIG. 5 is a perspective view of a pedestal weldment of the target pedestal assembly illustrated in FIG. 4.
Figure 6:
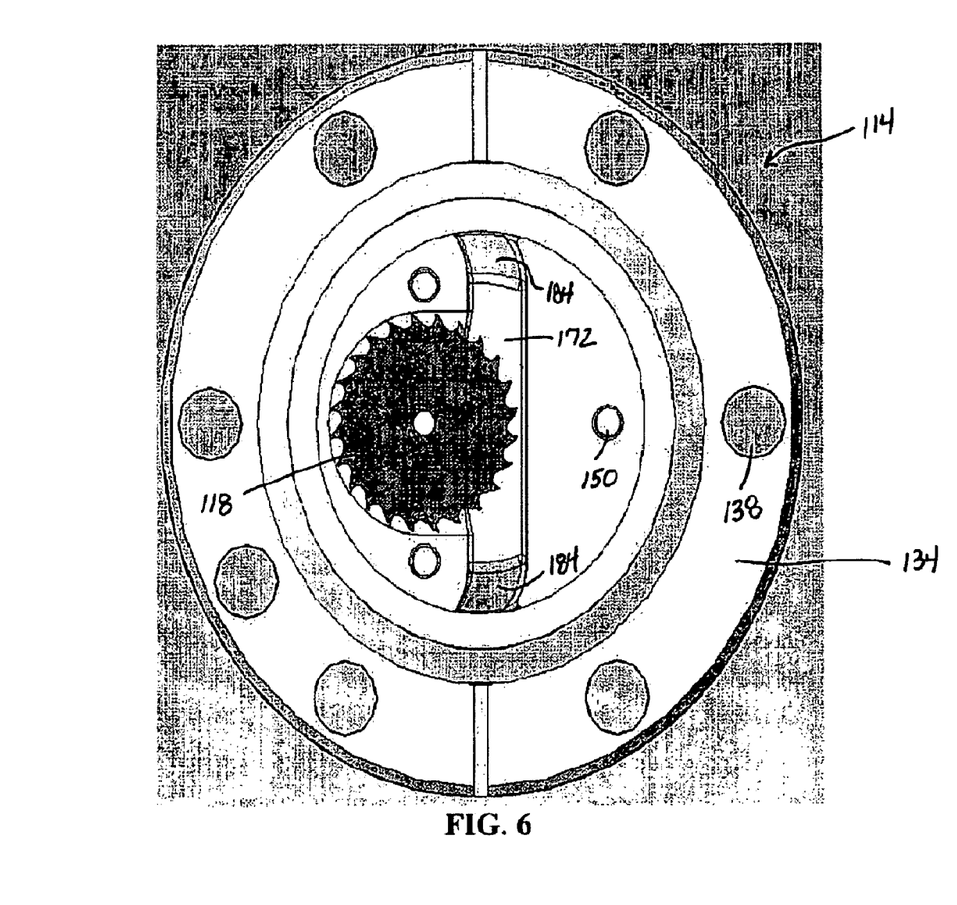
FIG. 6 is a top view of the pedestal weldment of the target pedestal assembly illustrated in FIG. 4.

The pedestal subassembly 114, further illustrated in FIGS. 5-6, can be brazed, welded, bolted or coupled together by suitable fasteners. The pedestal subassembly 114 includes a base 134 having a plurality of apertures 138 that allow for its attachment as part of the greater radiation therapy system 10. The pedestal weldment 114 also includes a raised portion 142 extending from the base 134 and generally centered within the base 134. The raised portion 142 includes a generally planar first surface 146 having a plurality of apertures 150 each adapted to receive one of the fasteners 130. The raised portion 142 also includes a second generally planar surface 154 defining a recess 156 formed within and non-co-planar with the first surface 146 and configured to receive the target 118. The recess 156 includes an aperture 160 and a raised portion 164 generally surrounding the aperture 160. The aperture 160 is offset from a center point of the raised portion 142. The aperture 160 is configured to receive the pin 122 such that the target 118 is rotationally secured within the recess 156 with the rotational pin 122.

The raised portion 142 also includes a third generally planar surface 168 at an elevation lower than the second surface 154 and defining a channel 172 formed within the first surface 146. A portion of the channel 172 is positioned adjacent to the recess 156 and includes a first end 176 and a second end 180. A portion of the target 118 is positioned over the channel 172 with a gap existing between the target 118 and the third surface 168 due to the third surface 168 being at a lower elevation than the second surface 154. The first end 176 and the second end 180 of the channel 172 include a ramped surface 184 extending gradually to a lower elevation than the third surface 168.

Figure 8:
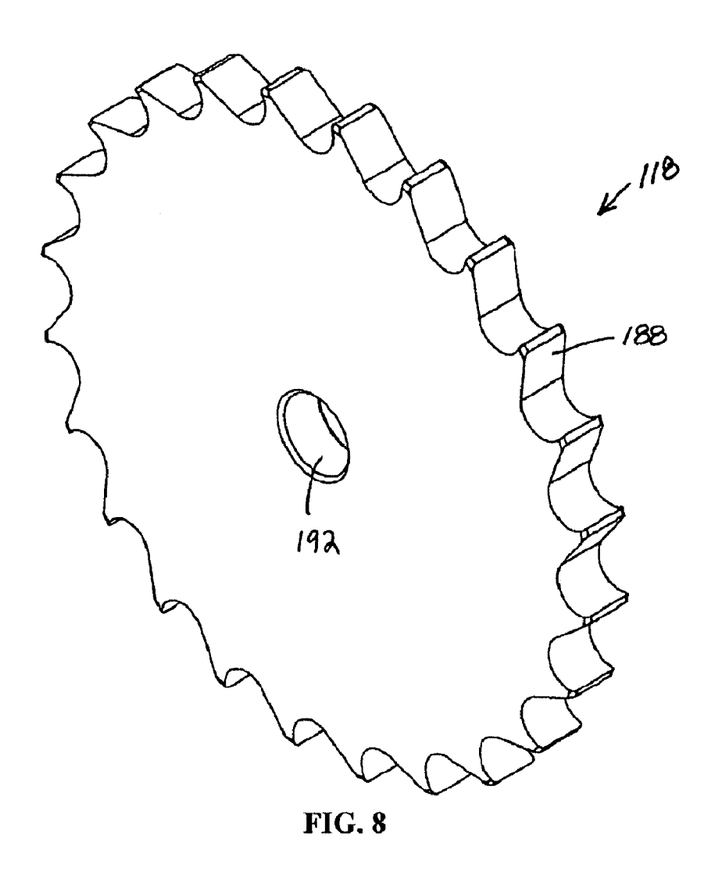
FIG. 8 is a perspective view of a target of the target pedestal assembly illustrated in FIG. 4.

The target 118, further illustrated in FIGS. 6 and 8, can include a serrated perimeter 188 and an aperture 192 at its center to accommodate the rotational pin 122. Although FIGS. 6 and 8 illustrate the target 118 having a serrated perimeter, the target 118 can include a smooth or other suitable shaped perimeter. The target 118 is comprised of a refractory metal with a high melting point such as tungsten, molybdenum, rhenium, or any suitable alloys, of the type that produce x-rays when impacted by a high energy electron beam 30. In one embodiment, the target 118 is a solid, disc-shaped piece of metal at least partially covered with a protective agent that has good thermoconductivity and little or no chemical reactivity, especially with the cooling fluid such as water or its components. The target 118 can be protected with various materials including diamond, chromium nitride, titanium nitride, or iridium.

The protective agent can be applied to the target 118 via several processes such as by physical vapor deposition. In one embodiment, a tungsten target is coated with chromium nitride through a physical vapor deposition process so that the coating is atomically bonded to the target material.

The target 118 also can be completely encased in a chemically resistant protective coating. The casing material may be bonded (e.g., brazing, spin-welding, other types of welding, plating, and explosive bonding) to the target 118. Various alloys could be used to encase the target, as well as chromium nitride, titanium nitride, or iridium, but in any embodiment, the casing material should be able to handle high amounts of radiation and should have little chemical reactivity to the cooling fluid and its decomposition products. When the casing material is brazed to the target 118, extra care must be taken to ensure that there is good thermal contact between the target 118 and the casing to make sure that heat is efficiently transferred from the target through the casing to the coolant.

Another way to protect the target is to braze a protective surface to a portion of the target 118 in order to spread out the heat generated at the point where the electron beam 30 impacts the target 118. The protective surface could be applied to the target 118 in an annulus or ring shape, for example, covering the path of the electron beam 30 about the rotating target 118. The protective surface on the target 118 may be applied outside the beam path. The protective surface can be made of any number of alloys, such as a zirconium alloy, that is capable of withstanding a significant amount of radiation. In some embodiments, both the top and the bottom surfaces of the target 118 may include a protective surface. In addition, some or all of the serrated edges of the target 118 can include a protective surface.

Coating, encasing, brazing, or otherwise covering the target 118 with a protective material facilitates steady rotation of the target. Even as the protective material degrades along the electron beam path 30, the protective material stays intact around the rotational pin 122, which is where rotational support occurs. Thus, the protective coating on the target 118 helps to keep rotation steady by maintaining the diameter of the aperture 192, spreading the heat evenly across the target 118, and prolonging target life.

Figure 9:
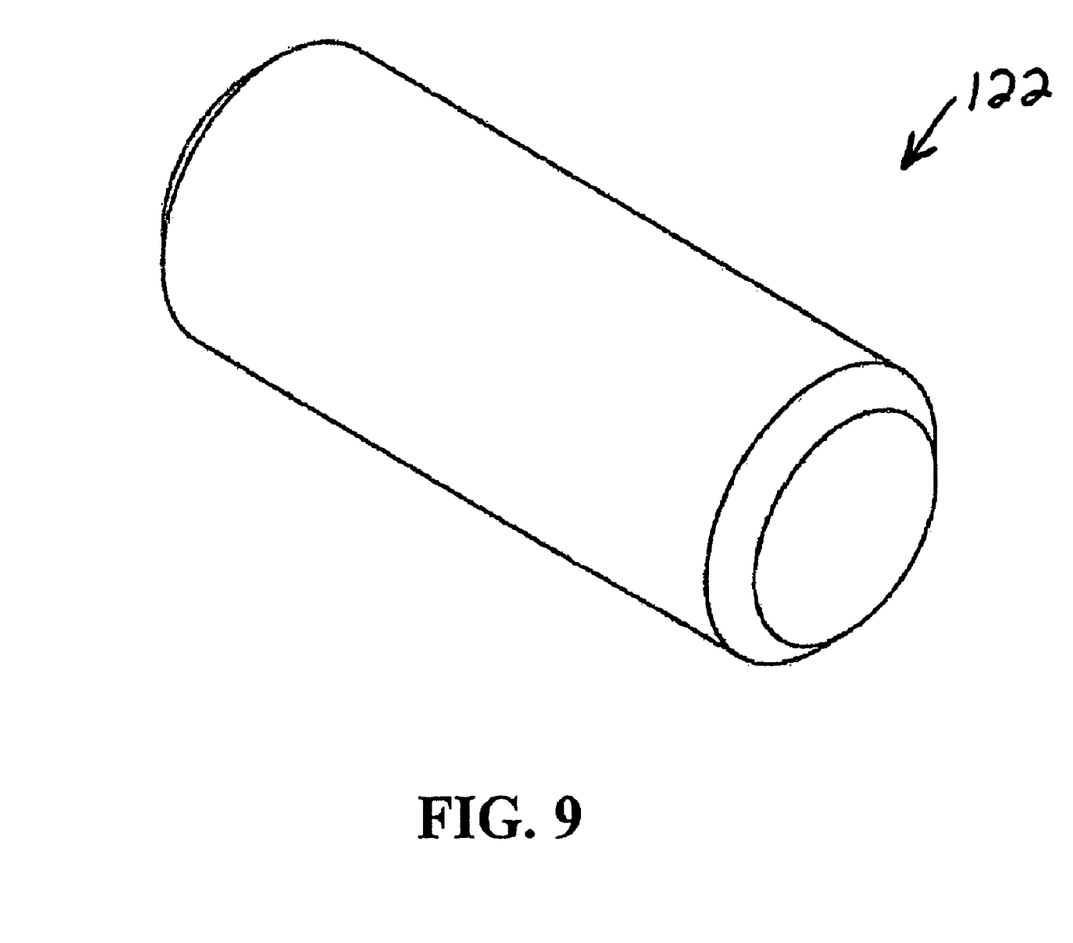
FIG. 9 is a perspective view of a pin of the target pedestal assembly illustrated in FIG. 3.

The rotational pin 122, further illustrated in FIG. 9, is configured to be received in the aperture 192 of the target 118 and the aperture 160 of the recess 156 to rotationally secure the target 118 to the pedestal weldment 114. The pin 122 includes a beveled edge at a first end and a second end thereof. The rotational pin 122 is replaceable, making possible refurbishment of the target pedestal assembly 102. The pin 122 has a high lubricity, which allows for high target rotational speeds with minimal wear of the target aperture 192. In one embodiment, the pin 122 is comprised of tungsten carbide, making it resistant to oxidation, thermal effects, and mechanical wear and making it superior to a stainless steel pin, which would mechanically wear due to continuous contact with, for example, a tungsten target.

The pin 122 includes a predetermined length to maintain a minimum gap between the raised portion 164 and raised portion 216. The gap prevents the target 118 from being pinched thereby slowing or eliminating rotation. The rotational pin 122 also protects the target 118 from the target cover 126 by supporting the target within the target cavity 202. The rotational pin 122 does not pass through the aperture 212 in the target cover 126. By keeping the pin 122 in the cover, it prevents the linac window from being punctured by the pin 122 and releasing the vacuum. Moreover, the target cover 126 gets hot when the electron beam is operating, and the cover may bow downward toward the target 118. The pin 122 supports the target cover such that even with the bowing the target cover does not contact the target 126 and high rotational speeds can be maintained.

Figure 7:
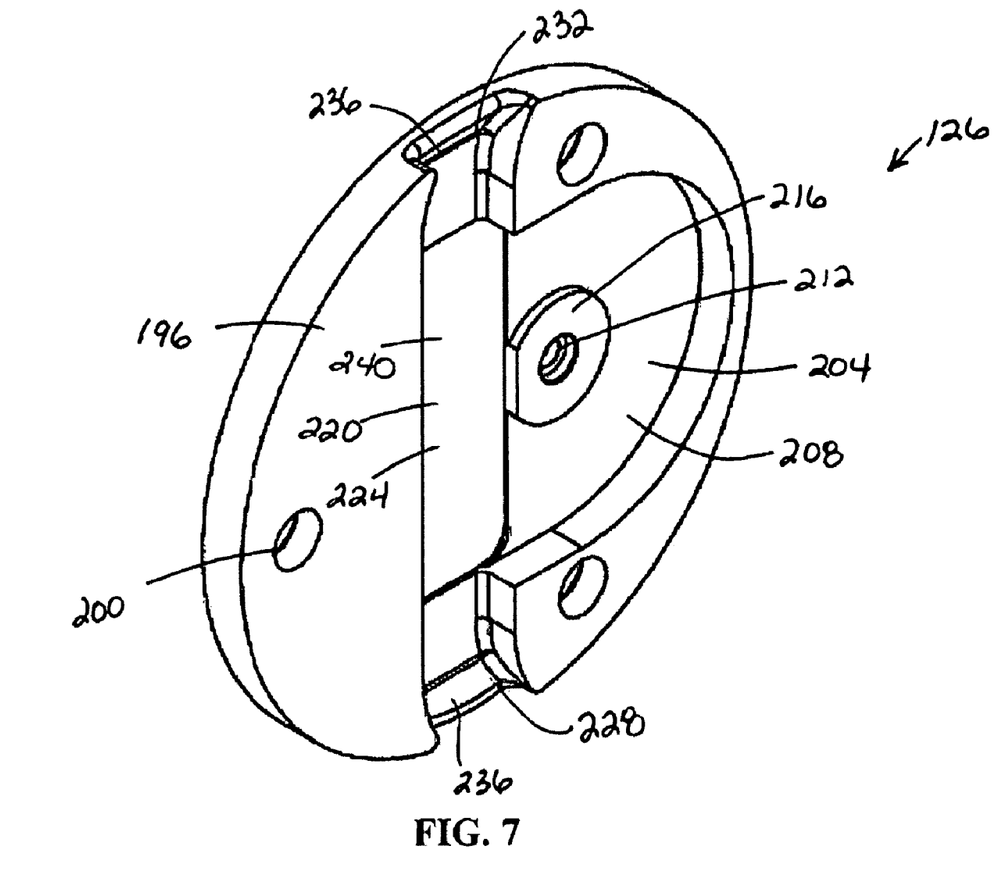
FIG. 7 is a perspective view of a cover of the target pedestal assembly illustrated in FIG. 4.

The cover 126, further illustrated in FIG. 7, includes a first generally planar surface 196 having a plurality of apertures 200 each adapted to receive one of the fasteners 130 to connect the target cover 126 to the pedestal weldment 114. The cover 126 also includes a second generally planar surface 204 defining a recess 208 formed within the first surface 196 and configured to receive the target 118. The recess 208 includes an aperture 212 and a raised portion 216 generally surrounding the aperture 212. The aperture 212 is offset from a center point of the cover 126 and is substantially aligned with the aperture 160 on the pedestal weldment 114 when the cover 126 is attached thereto. The aperture 212 is configured to receive one end of the pin 122 such that the target 118 is rotationally secured within the recess 208 with the rotational pin 122. The recess 208 of the cover 126 and the recess 156 of the pedestal weldment 114 form a cavity 202 (illustrated in FIGS. 4 and 10) in which the target 118 is configured to rotate when the cover 126 is connected to the pedestal weldment 114.

The cover 126 also includes a third generally planar surface 220 at an elevation lower than the second surface 204 and defining a channel 224 formed within the first surface 196. A portion of the channel 224 is positioned adjacent to the recess 208 and includes a first end 228 and a second end 232. A portion of the target 118 is positioned over the channel 224 with a gap existing between the target 118 and the third surface 220 due to the third surface 220 being at a lower elevation than the second surface 204. The first end 228 and the second end 232 of the channel 224 include a ramped surface 236 extending gradually to a higher elevation than the third surface 220. The cover 126 also includes a window 240 positioned within the channel 224 and between the first end 228 and the second end 232.

Figure 10:
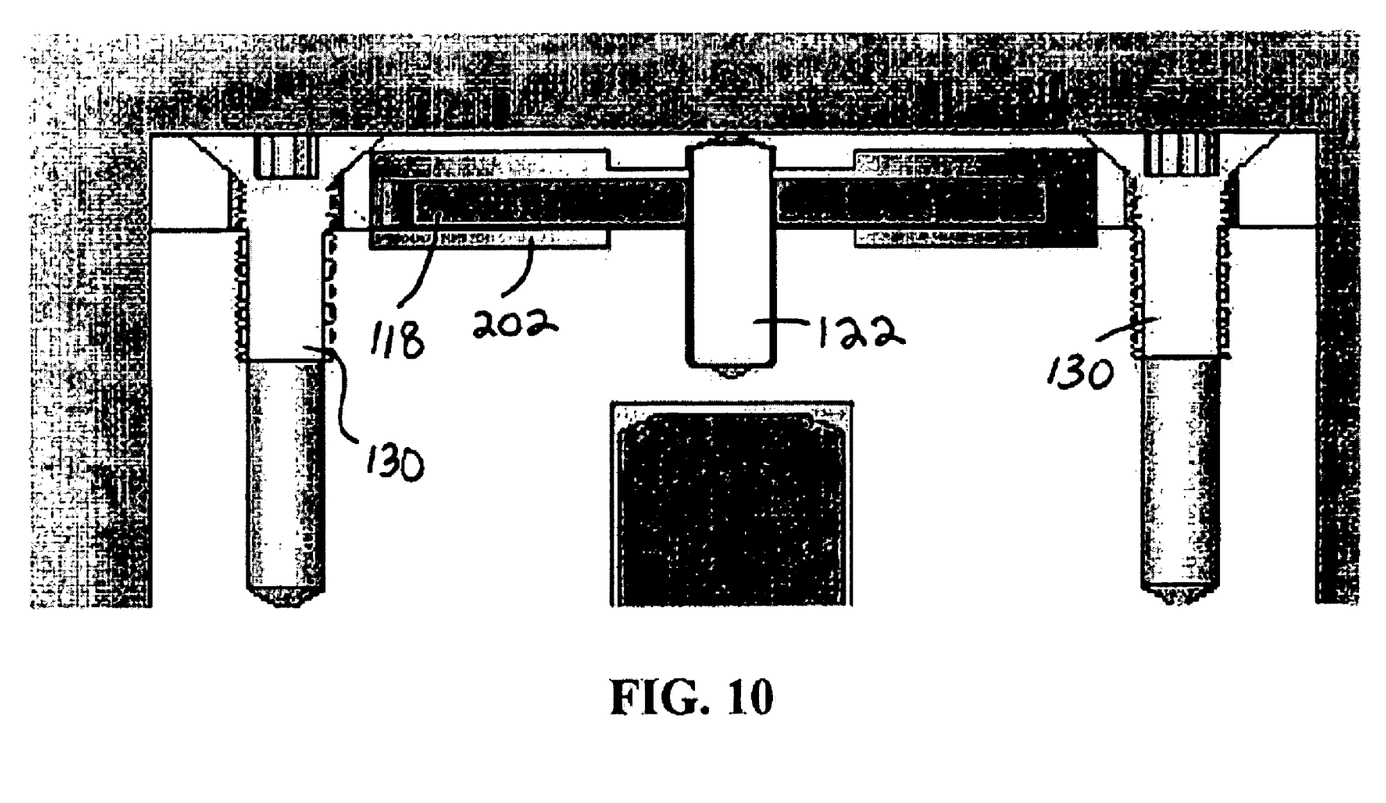
FIG. 10 is a cross-sectional view of the target pedestal assembly illustrated in FIG. 4.
Figure 11:
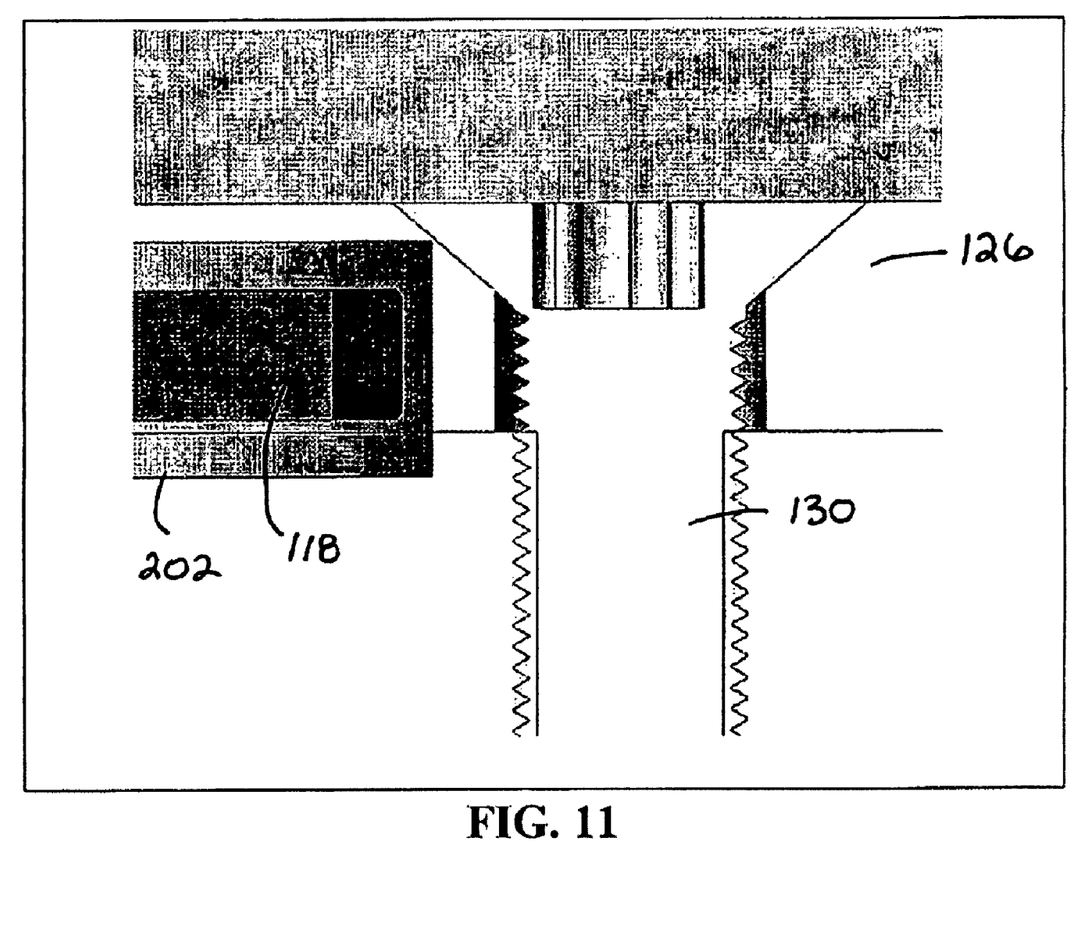
FIG. 11 is an enlarged cross-sectional view of a portion of the target pedestal assembly illustrated in FIG. 10.

As discussed above, the cover 126 is connected to the pedestal weldment 114 with the plurality of fasteners 130. As illustrated in FIGS. 10-11, the fasteners 130, such as 100 degree flat head screws, and counter sink do not break through the cavity 202 and thus cannot impede target rotation. FIG. 10 further illustrates a side view of the cavity 202, the target 118, and the pin 122. The rotational pin 122 does not extend through the target cover 126.

As illustrated in FIG. 7, the ramped surfaces 236 at the first end 228 and the second end 232 form integrated flow diverters which direct the flow of cooling fluid (e.g., water) to and around the target 118 and support a generally straight tangential, parallel flow of cooling fluid across the target 118. The integrated flow diverters guide the flow of cooling fluid to and around the target 118. The flow diverters push the fluid flow to the perimeter of the target 118, engaging the target's serrated edges for better rotation, while at the same time not reducing the coolant flow across the target surface that is being impacted by the electron beam 30. The target 118 can achieve higher rotational speeds, such as about 3800-4100 RPM, when the cover 126 with integrated flow diverters are used as compared to speeds of only 1800 RPM with a partial target cover lacking the flow diverters.

The use of the target cover 126 with integrated flow diverters allows for flattening of the coolant flow while keeping consistent flow across the top and bottom surfaces of the target 118. The ramped surfaces 236 guide the cooling fluid as it either enters or exits the target cavity 202. Water is circulated through the flow diverters and over the target 118. The water or other coolant fluid cools the target 118 because the heat generated by the electron beam contacting the target is transferred from the target to the flowing water. The ducted, parallel fluid flow with the flow diverters reduces out-of-plane torque on the target 118, which aids in consistent rotation of the target, as out-of-plane torque can impede rotation. The parallel movement of the fluid reduces the tendency of the target 118 to tip and jam, thereby allowing for high rotational speed.

To produce x-rays as part of the radiation therapy system 10, the linear accelerator 26 produces a high-energy electron beam 30 that moves through a linac exit window. The electron beam 30 is aimed at the target 118 to produce x-ray radiation. The target 118 can be integral to the linac 26, or it may be housed outside the linac's vacuum environment. In one construction, the target 118 is external to the linac 26 and is supported by the target pedestal assembly 102.

In operation and according to one embodiment, the electron beam 30 impacts the target near the serrated edge of the target 118. The target 118 is at least partially positioned between the fluid channel 172, 224 such that the serrated edge of the target 118 engages the flow of cooling fluid across the target 118 like paddle wheels, resulting in the passive rotation of the target 118. Rotation is passive because it is achieved by a viscous drag of the coolant on the target 118 surface and/or by momentum transfer of the coolant on the serrated edge. The target 118 can rotate in order to spread out the electron beam pulses, prevent overlap of those pulses, and allow for adequate dissipation of heat to preserve the target 118. As the target 118 rotates, the electron beam 30 contacts the target 118 in a circular path rather than at only a singular impact point, as would be the case with a stationary target. The target cover 126 directs the flow of cooling fluid through the channel 172, 224 such that the target 118 is submerged in the cooling fluid. The electron beam 30 passes through the fluid. The fluid moves in direct contact with the target 118 with a flow that is substantially parallel to the target 118 and provides a protected environment to allow for consistent rotation of the target 118. This directed, controlled flow allows for high target rotational speed of the target 118 and for heat transfer away from the target 118.

Still other embodiments are within the scope of the invention. For example, water is not the only coolant that may be used in the target-cooling system. Moreover, having described several embodiments of the invention with reference to the accompanying drawings, it is to be understood that the invention is not limited to those precise embodiments and that various changes and modifications may be effected therein by one skilled in the art without departing from the scope or spirit of the invention as defined in the claims. A number of modifications may be made to the present invention without departing from the inventive concept therein.

Various features and advantages of the invention are set forth in the following claims.

What is claimed is:

1. A target pedestal assembly for a radiation delivery device, the target pedestal assembly comprising:
   a pedestal subassembly coupled to a linear accelerator of the radiation delivery device, the pedestal subassembly including a first recessed area and an aperture positioned within the first recessed area;
   a cover coupled to the pedestal subassembly, the cover including a second recessed area complementary to the first recessed area, the second recessed area including an aperture positioned within the second recessed area, the aperture not extending through the cover;
   a target including an aperture therethrough; and
   a pin configured to receive the target through the aperture, to be received within the aperture of the pedestal subassembly, to be received within the aperture of the cover, and to position the target between the first recessed area of the pedestal subassembly and the second recessed area of the cover, the pin further configured to prevent the target from being pinched by one of the first recessed area and the second recessed area.

2. The target pedestal assembly of claim 1 wherein the pin is configured to rotationally couple the target to the pedestal subassembly and the cover.

3. The target pedestal assembly of claim 1 wherein the pin includes a length configured to maintain a minimum gap between the target and the second recessed area of the cover and between the target and the first recessed area of the pedestal subassembly.

4. The target pedestal assembly of claim 1 wherein the pin comprises tungsten carbide.

5. The target pedestal assembly of claim 1 wherein the pedestal subassembly includes a first channel adjacent to the first recessed area, the first channel including a first flow diverter at a first end of the channel and a second flow diverter at a second end of the channel.

6. The target pedestal assembly of claim 5 wherein the cover includes a second channel complementary to the first channel, the second channel including a first flow diverter at a first end of the channel and a second flow diverter at a second end of the channel.

7. The target pedestal assembly of claim 6 wherein a portion of the target is positioned between the first channel and the second channel, at least a portion of the target being protected with a material sufficient to reduce chemical reactivity between the target and a cooling medium or its decomposition products flowing in the channel.

8. The target pedestal assembly of claim 7 wherein the cooling medium flowing within the first channel and the second channel propels rotation of the target.

9. The target pedestal assembly of claim 8 wherein flow of the cooling medium within the first channel and the second channel is substantially co-planar with the target.

10. The target pedestal assembly of claim 9 wherein the target rotates at a speed of about greater than about 2000 RPM.

11. The target pedestal assembly of claim 7 wherein the cooling medium is water.

12. The target pedestal assembly of claim 7 wherein the target protection is a coating material.

13. The target pedestal assembly of claim 12 wherein the coating material comprises chromium nitride.

14. The target pedestal assembly of claim 12 wherein the coating material is atomically bonded to the target through a physical vapor deposition process.

15. The target pedestal assembly of claim 12 wherein the coating material is applied to the entire target.

16. The target pedestal assembly of claim 12 wherein the radiation delivery device delivers a beam of radiation to the target along a beam path, and wherein the coating material is applied to a portion of the target outside of the beam path.

17. The target pedestal assembly of claim 7 wherein the target protection is a casing material comprising a material suitable for handling high amounts of radiation and low chemical reactivity to cooling medium or its decomposition product.

18. The target pedestal assembly of claim 17 wherein the casing material is bonded to the target.

19. The target pedestal assembly of claim 7 wherein the target protection is a protective surface applied to a portion of the target.

20. The target pedestal assembly of claim 19 wherein the protective surface is at a location where the target receives an electron beam.

21. A target pedestal assembly for a radiation delivery device, the target pedestal assembly comprising:
   a housing coupled to a linear accelerator of the radiation delivery device, the housing defining a cavity and a channel adjacent to the cavity, the channel including a first flow diverter at a first end of the channel and a second flow diverter at a second end of the channel;
   a target positioned within the cavity and rotationally coupled to the housing, a portion of the target positioned within the channel, the target including a serrated edge arranged around a perimeter of the target; and
   a cooling medium positioned within the cavity and the channel, the target being protected with a material sufficient to reduce chemical reactivity between the target and the cooling medium.

22. The target pedestal assembly of claim 21 further comprising a pin configured to rotationally couple the target to the housing.

23. The target pedestal assembly of claim 22 wherein the pin includes a length configured to maintain a minimum gap between the target and the housing.

24. The target pedestal assembly of claim 22 wherein the pin comprises tungsten carbide.

25. The target pedestal assembly of claim 21 wherein the cooling medium flowing within the channel propels rotation of the target.

26. The target pedestal assembly of claim 25 wherein flow of the cooling medium within the channel is substantially co-planar with the target.

27. The target pedestal assembly of claim 26 wherein the target rotates at a speed greater than about 2,000 RPM.

28. The target pedestal assembly of claim 21 wherein the target protection is a coating material.

29. The target pedestal assembly of claim 28 wherein the coating material comprises chromium nitride.

30. The target pedestal assembly of claim 28 wherein the coating material is atomically bonded to the target through a physical vapor deposition process.

31. The target pedestal assembly of claim 21 wherein the target protection is a casing material comprising a material suitable for handling high amounts of radiation and low chemical reactivity to the cooling medium or its decomposition product.

32. The target pedestal assembly of claim 31 wherein the casing material is brazed to the target.

33. The target pedestal assembly of claim 21 wherein the target protection is a protective surface applied to a portion of the target.

34. The target pedestal assembly of claim 33 wherein the protective surface is at a location where the target receives an electron beam.

35. The target pedestal assembly of claim 34 wherein the cooling medium is water.

36. A target pedestal assembly for a radiation delivery device, the target pedestal assembly comprising:
   a housing including a cavity and a cooling medium flowing within the cavity; and
   a target comprising tungsten and positioned within the cavity, the target submerged in the cooling medium, the target being protected with a material sufficient to reduce chemical reactivity between the target and the cooling medium, and
   wherein the cooling medium flowing within the cavity propels rotation of the target.

37. The target pedestal assembly of claim 36 further comprising a pin configured to rotationally couple the target to the housing.

38. The target pedestal assembly of claim 37 wherein the pin includes a length configured to maintain a minimum gap between the target and the housing.

39. The target pedestal assembly of claim 37 wherein the pin comprises tungsten carbide.

40. The target pedestal assembly of claim 36 wherein flow of the cooling medium within the cavity is substantially co-planar with the target.

41. The target pedestal assembly of claim 40 wherein the target rotates at a speed greater than about 2,000 RPM.

42. The target pedestal assembly of claim 36 wherein the target protection is a coating material.

43. The target pedestal assembly of claim 42 wherein the coating material comprises chromium nitride.

44. The target pedestal assembly of claim 42 wherein the coating material is atomically bonded to the target through a physical vapor deposition process.

45. The target pedestal assembly of claim 36 wherein the target protection is a casing material comprising a material suitable for handling high amounts of radiation and low chemical reactivity to the cooling medium or its decomposition product.

46. The target pedestal assembly of claim 45 wherein the casing material is brazed to the target.

47. The target pedestal assembly of claim 36 wherein the target protection is a protective surface applied to a portion of the target.

48. The target pedestal assembly of claim 47 wherein the protective surface is at a location where the target receives an electron beam.

49. The target pedestal assembly of claim 48 wherein the cooling medium is water.

50. A target pedestal assembly for a radiation delivery device, the target pedestal assembly comprising:
a housing including a cavity and a cooling medium flowing within the cavity; and
a target comprising tungsten and positioned within the cavity, the target submerged in the cooling medium, the target being protected with a material sufficient to reduce chemical reactivity between the target and the cooling medium; and
a pin configured to rotationally couple the target to the housing.

51. The target pedestal assembly of claim 50 wherein the pin includes a length configured to maintain a minimum gap between the target and the housing.

52. The target pedestal assembly of claim 50 wherein the pin comprises tungsten carbide.

* * * * *